(12) United States Patent
Buske et al.

(10) Patent No.: US 10,739,023 B2
(45) Date of Patent: Aug. 11, 2020

(54) VENTILATION SYSTEM AND METHOD FOR OPERATING IT

(71) Applicant: PlasmaTreat GmbH, Steinhagen (DE)

(72) Inventors: Christian Buske, Bielefeld (DE); Daniel Hasse, Paderborn (DE)

(73) Assignee: PlasmaTreat GmbH, Steinhagen (DE)

( * ) Notice: Subject to any disclaimer, the term of this patent is extended or adjusted under 35 U.S.C. 154(b) by 0 days.

(21) Appl. No.: 15/531,869

(22) PCT Filed: Nov. 30, 2015

(86) PCT No.: PCT/EP2015/078033
§ 371 (c)(1),
(2) Date: May 31, 2017

(87) PCT Pub. No.: WO2016/087357
PCT Pub. Date: Jun. 9, 2016

(65) Prior Publication Data
US 2017/0276381 A1   Sep. 28, 2017

(30) Foreign Application Priority Data

Dec. 1, 2014   (DE) .......................... 10 2014 117 624

(51) Int. Cl.
*A61L 9/015* (2006.01)
*F24F 3/16* (2006.01)
(Continued)

(52) U.S. Cl.
CPC ............... *F24F 3/16* (2013.01); *A61L 2/202* (2013.01); *A61L 2/24* (2013.01); *A61L 2/26* (2013.01);
(Continued)

(58) Field of Classification Search
CPC .................................. F24F 3/16; A61L 9/205
See application file for complete search history.

(56) References Cited

U.S. PATENT DOCUMENTS

| 5,433,927 A * | 7/1995 | Mausgrover ............ C01B 13/11 |
| | | 422/186.07 |
| 2004/0146437 A1* | 7/2004 | Arts ......................... A61L 2/10 |
| | | 422/186.07 |

(Continued)

FOREIGN PATENT DOCUMENTS

| CN | 101130100 A | 2/2008 |
| DE | 10313385 A1 | 10/2004 |

(Continued)

OTHER PUBLICATIONS

Matsunaga et al. JP 2005-056647 . Mar. 3, 2005 (English Machine Translation). (Year: 2005).*

*Primary Examiner* — Donald R Spamer
(74) *Attorney, Agent, or Firm* — The Webb Law Firm

(57) ABSTRACT

A ventilation system includes a line system which is designed to guide an air stream and to provide the air stream during normal operation via an outlet of the line system for supplying a space. The ventilation system includes a generating unit which is designed to produce reactive oxygen species during a cleaning operation and to feed the same to the air stream conducted in the line system. Also disclosed are methods for operating such a ventilation system and a generating unit for such a ventilation system.

13 Claims, 5 Drawing Sheets

(51) Int. Cl.
*H05H 1/48* (2006.01)
*A61L 2/20* (2006.01)
*A61L 2/24* (2006.01)
*A61L 2/26* (2006.01)
*C01B 13/11* (2006.01)
*A61L 9/22* (2006.01)

(52) U.S. Cl.
CPC ............ *A61L 9/015* (2013.01); *C01B 13/115* (2013.01); *H05H 1/48* (2013.01); *A61L 9/22* (2013.01); *A61L 2202/11* (2013.01); *A61L 2202/13* (2013.01); *A61L 2202/14* (2013.01); *A61L 2209/14* (2013.01); *A61L 2209/211* (2013.01); *A61L 2209/212* (2013.01); *C01B 2201/90* (2013.01); *F24F 2003/1664* (2013.01); *F24F 2003/1671* (2013.01); *F24F 2003/1692* (2013.01); *F24F 2221/22* (2013.01); *H05H 2245/121* (2013.01)

(56) References Cited

U.S. PATENT DOCUMENTS

| | | | |
|---|---|---|---|
| 2005/0124286 A1* | 6/2005 | Goldsmith | A61L 9/015 454/157 |
| 2005/0199484 A1* | 9/2005 | Olstowski | C01B 13/11 204/176 |
| 2008/0163754 A1 | 7/2008 | Tanaka et al. | |
| 2011/0179951 A1 | 7/2011 | Suzuki et al. | |
| 2012/0207647 A1* | 8/2012 | Kim | A61L 9/22 422/107 |
| 2014/0322085 A1* | 10/2014 | Hoffman | A61L 2/00 422/119 |

FOREIGN PATENT DOCUMENTS

| | | |
|---|---|---|
| DE | 202006016535 U1 | 4/2007 |
| DE | 102006049320 A1 | 4/2008 |
| EP | 1666152 A1 | 6/2006 |
| EP | 2154440 A2 | 2/2010 |
| EP | 2301588 A1 | 3/2011 |
| JP | 2302536 A | 12/1990 |
| JP | 31024 A | 1/1991 |
| JP | 3160231 A | 7/1991 |
| JP | 200556647 A | 3/2005 |
| JP | 200849002 A | 3/2008 |
| WO | 2007061295 A1 | 5/2007 |

* cited by examiner

VENTILATION SYSTEM AND METHOD FOR OPERATING IT

CROSS-REFERENCE TO RELATED APPLICATIONS

This application is the United States national phase of International Application No. PCT/EP2015/078033 filed Nov. 30, 2015, and claims priority to German Patent Application No. 102014117624.3 filed Dec. 1, 2014, the disclosures of which are hereby incorporated in their entirety by reference.

BACKGROUND OF THE INVENTION

Field of the Invention

The invention relates to a ventilation system, in particular an air-conditioning system, having a piping system which is configured to convey an air flow and to provide the air flow via an outlet of the piping system for supplying a room during a normal operation. The invention also relates to the use of such a ventilation system and to a method for operating it.

Description of Related Art

Ventilation and air-conditioning systems are in particular used in building technology to provide rooms with fresh air and/or to air-condition them. When operating such systems, one is, however, faced with the problem that they can in time become contaminated with dirt or germs, whereby, on the one hand, the proper functioning of these systems is impaired and, on the other hand, a considerable health risk can develop for persons staying in the ventilated or air-conditioned rooms.

This is particularly problematic if the ventilation or air-conditioning systems are used to ventilate or air-condition operating theatres or other rooms which have to be kept sterile. Thus, even a slight contamination of the ventilation system with germs can result in such an operating theatre being contaminated and hence in an increased risk of infection for patients treated there, which in extreme cases can even be life-threatening.

For this reason, in many countries there are strict hygiene requirements for ventilation and air-conditioning systems and devices which are used in hospitals. In Germany, these requirements are defined, for example, in DIN 1946 Part 4 and in VDI standard 6022.

In order to prevent air-conditioning systems and ventilation systems from becoming contaminated by germs, in the prior art, samples are regularly taken in the systems and tested for increased germ values. If a contamination is determined with such a measurement, then maintenance and cleaning of the corresponding ventilation or air-conditioning system is ordered. However, this procedure has several disadvantages. Firstly, in the times between the sample takings, an incipient contamination with germs can remain undiscovered. Secondly, maintenance and cleaning of the air-conditioning system can often not take place immediately, whereby the cleaning is delayed and the risk of infection is increased. Finally, the cleaning and maintenance of air-conditioning and ventilation systems, which is often carried out by specialist companies, requires a not inconsiderable amount of time and effort and regularly requires a temporary closure of the room supplied by the ventilation or air-conditioning system. A closure of an operating theatre for 24 hours can occur as a result of this, for example, whereby high non-use times and costs, as well as capacity shortages, result.

Against this background, the invention is based on an object of providing a ventilation system, by means of which the previously mentioned problems can be at least partly overcome.

SUMMARY OF THE INVENTION

This object is, in the case of a ventilation system, in particular an air-conditioning system, having a piping system which is configured to convey an air flow and to provide the air flow via an outlet of the piping system for supplying a room during a normal operation, according to the invention at least partly achieved by the ventilation system having a generating unit which is configured to generate reactive oxygen species during a cleaning operation and to feed them to the air flow conveyed in the piping system.

In addition, the previously mentioned object is achieved by a method for operating the previously mentioned ventilation system, in particular air-conditioning system, in which an air flow is conveyed in the piping system and is provided via the outlet for supplying a room, in particular is fed to a room, during a normal operation, and in which during a cleaning operation reactive oxygen species are generated by means of the generating unit and fed to an air flow conveyed in the piping system.

It was found that the hygiene and the operation of ventilation or air-conditioning systems can be improved by integrating a generating unit for generating reactive oxygen species directly into such a ventilation or air-conditioning system. In this way, the ventilation or air-conditioning system can be disinfected at regular intervals or even sterilised, so that contamination by germs is eliminated or cannot even occur in the first place.

According to DIN EN 1040, a disinfection is understood as a reduction in the number of germs by at least 5 decimal logarithmic levels for bacteria and by at least 4 decimal logarithmic levels for viruses. According to DIN EN 556, a sterilisation is understood as a reduction in the number of germs by at least 6 decimal logarithmic levels (for viruses and bacteria).

The ventilation system has a piping system which is configured to convey an air flow. Such a piping system typically comprises pipes, by means of which an air flow can be conveyed from one place, for example from a heat exchanger of an air-conditioning system, a central air supply or an air intake opening, for example on the outside of a building, to another place, in particular to an outlet opening, which opens into a room to be supplied with the air flow. The piping system can also have means for propelling the air, such as rotors or nozzles, in order to produce or maintain the air flow in the piping system.

The piping system is also configured to provide the air flow via an outlet of the piping system for supplying a room during a normal operation. For this purpose, the piping system typically has an outlet opening, by means of which the piping system can be attached to a corresponding through hole in a room to be supplied, for example to a ventilation opening in a wall of a room. Normal operation is in the present case understood as the normal ventilation operation or air-conditioning operation of the ventilation or air-conditioning system.

The ventilation system has a generating unit which is configured to generate reactive oxygen species during a cleaning operation. A cleaning operation is in the present case understood as an alternative operating mode to the normal operation of the ventilation system, which serves to clean, disinfect or sterilise the ventilation system.

Reactive oxygen species (ROS) are understood as reactive forms of the oxygen which have a damaging effect on microorganisms and are therefore suitable for the disinfection and sterilisation. Typical examples for reactive oxygen species are: superoxide anions ($O_2$—), superoxide anion radicals ($O_2.$—, hydroxy radicals (HO.), hydroperoxide radicals (HOO.), peroxy radicals (ROO.), alkyl radicals (RO.), hydrogen peroxide ($H_2O_2$), hydroperoxide (ROOH), ozone ($O_3$), hypochloride anions (OCl—), singlet oxygen ($^1O_2$) or nitrogen compounds, such as $NO_2+$, NO— etc. Preferably, primarily peroxides and ozone, which have a good disinfection and sterilisation effect, are generated as reactive oxygen species during the cleaning operation.

The term "microorganisms" used in the present case, besides microorganisms in the strict sense, also comprises cellular or non-cellular biological material which is able to multiply or pass on genetic material. In addition, according to CEN 12740, biological material which can cause infections and allergies or has a toxic effect is also included. According to these definitions, viruses, viroids, parasites, cells consisting of multicellular plant and animal organisms, prions and plasmids are also included under the term microorganisms.

By integrating the generating units into the ventilation system, these reactive oxygen species can be generated directly when in the desired quantity. This is particularly advantageous compared to a provisioning and release of reactive oxygen species when needed, since the oxygen species which are particularly effective for the disinfection or sterilisation have a short half-life and in storage quickly change into less reactive species. In particular, the ventilation system can be configured in such a way that the propagation of the ROS occurs in an optimum way by being able to adapt both the number and the position of the generating units. A local and optimum propagation of the ROS is thereby ensured.

Various embodiments of the ventilation system and of the method for operating it are described below, wherein the individual embodiments are applicable both for the ventilation system and for the method. The individual embodiments can also be combined with one another.

According to a first embodiment, the ventilation system has a control which is configured to control the generating unit in such a way that during a cleaning operation a concentration of reactive oxygen species of at least 7 $g/m^3$, preferably of at least 10 $g/m^3$, is achieved in an air flow conveyed in the piping system. Preferably, the control is configured to control the generating unit in such a way that during a cleaning operation an ozone concentration of at least 7 $g/m^3$, preferably of at least 10 $g/m^3$, is achieved in an air flow conveyed in the piping system. It was found that with a concentration of the reactive oxygen species, or in particular with a concentration of ozone, of at least 7 $g/m^3$ the ventilation system can be sufficiently disinfected. The ventilation system can be sufficiently sterilised with a concentration of the reactive oxygen species or of the ozone of at least 10 $g/m^3$.

According to a further embodiment, the ventilation system has a control which is configured to operate the ventilation system in cleaning operation at pre-specified times and/or for pre-specified periods. For example, the control can be configured to operate the ventilation system for a period of, for example, one hour during the night, so that the ventilation system is cleaned and sterilised every night and is thereby available clean and ready for operation on the next morning. In this way, the ventilation system can be operated smoothly with low maintenance. In addition, times when the rooms supplied by the ventilation system are out of use can be avoided.

According to a further embodiment, the control is configured to operate the generating unit in phases during the cleaning operation. Operating in phases is understood as the generating unit not generating reactive oxygen species during the whole cleaning operation, but rather as the cleaning operation also comprising at least one, preferably a plurality of, decaying periods, during which the generating unit does not generate any reactive oxygen species. It has been found that the reactive oxygen species have a certain life time before they are converted or transformed to the extent that their concentration is no longer sufficient for further effective disinfection. Therefore, it is not necessary to operate the generating unit during the whole cleaning operation, so that energy costs can be saved.

Preferably, the cleaning operation can have a plurality of activation periods, during which reactive oxygen species are generated using the generating unit, wherein the activation periods are interrupted by decaying periods, during which no further reactive oxygen species are generated. A concentration of reactive oxygen species consistently sufficient for the disinfection operation was achieved in tests, for example, with activation periods of 10 minutes in each case and subsequent decaying periods of 20 minutes in each case.

According to a further exemplary embodiment, the piping system can be switched between an air supply mode and an air circulation mode, wherein the piping system in the air supply mode is configured to provide an air flow conveyed in the piping system via the outlet for supplying a room, and wherein the piping system in the air circulation mode is configured to circulate an air flow conveyed in the piping system within the piping system. In a corresponding embodiment of the method, the air flow is circulated within the piping system during the cleaning operation. Preferably, the ventilation system has a control which is configured to switch the piping system into the air circulation mode during the cleaning operation.

It has been found that the ventilation system and the air-conditioning system can in particular be cleaned more effectively by circulating the air flow enriched with reactive oxygen species within the piping system without the air flow leaving the piping system. On the one hand, the duration of the cleaning operation or the duration of activation periods can hereby be shortened and, on the other hand, reactive oxygen species, in particular ozone, getting out of the piping system and in this way resulting in a health hazard or smell pollution in the room to be supplied is prevented.

In order to switch between the air supply mode and the air circulation mode, the piping system can, for example, have controllable air guiding elements, such as closable openings or valves, by means of which the air flow conveyed in the piping system can be conveyed through different pipe sections. By opening and closing certain air guiding elements, the piping system can in this way be switched back and forth between an air supply mode and an air circulation mode.

The cleaning operation can alternatively also be operated in the air supply mode. If the ventilation system, for example, in addition to an outlet also has an inlet, which is configured to suck an air flow out of the room to be supplied, then the circular flow of the air flow enriched with reactive oxygen species can also be closed via the room to be supplied, so that the air flow gets from the piping system through the outlet into the room to be supplied and from there gets into the piping system again through the inlet. In this way, the room to be supplied, for example a room of a building, in particular an operating theatre, a quarantine room on an isolation ward (isolation unit), a clean room or a laboratory room, or an interior of a closed device, such as an interior of a laboratory device (in particular of an incubator for cell and tissue cultures) or of a household appliance (in particular of a refrigerator etc.) can in particular also be at least partly disinfected or even sterilised.

According to a further embodiment, a feed is provided on the generating unit which is configured to feed in an additive to the generating unit. In particular, the feed can be configured to feed in water or steam or another additive, for example as powder or as an aerosol, to the generating unit. The types, the quantities and/or the distribution of the reactive oxygen species generated during operation of the generating unit can be influenced by means of the feed.

According to a further embodiment, the generating unit is configured to generate reactive oxygen species by means of an electrical discharge in a working gas, preferably by means of a dielectric barrier discharge. Reactive oxygen species can be generated in sufficient concentration when needed by means of such an electrical discharge without, in addition to an electrical supply, requiring complex infrastructure for operating the generating unit. A dielectric barrier discharge has proved to be particularly suitable for generating reactive oxygen species. Here, a high-frequency high voltage is applied between two electrodes, wherein a dielectric arranged between the electrodes impedes a direct discharge between the electrodes.

According to a further embodiment, the ventilation system comprises a device for reducing an ozone concentration which is configured to reduce the ozone concentration of the air flow conveyed in the piping system, preferably to a value below 0.1 ppm. One or more ceramic filters and/or activated carbon filters can be provided as the device for reducing an ozone concentration.

Furthermore, a plasma nozzle for generating an atmospheric plasma jet is also possible as the device for reducing an ozone concentration. Therefore, according to one embodiment, the ventilation device comprises a plasma nozzle for generating an atmospheric plasma jet, wherein the plasma nozzle is configured to generate the plasma jet by generating an arc discharge by applying a high-frequency high voltage between two electrodes in a working gas, and the piping system and the plasma nozzle are configured in such a way that the air flow conveyed in the piping system can be fed to the plasma nozzle as working gas.

A high-frequency high voltage is typically understood as a voltage of 1 to 100 kV, in particular of 1 to 50 kV, preferably of 10 to 50 kV, at a frequency of 1 to 350 kHz, preferably 1 to 100 kHz, particularly preferably 10 to 100 kHz, in particular of 10 to 50 kHz. The high-frequency high voltage can be a high-frequency alternating current voltage, but it can also be a pulsed direct current voltage.

An atmospheric plasma jet generated in this way has a high reactivity at relatively low temperature. In addition, the plasma jet generated in this way has only a very low ozone concentration and it was recognised that by generating such a plasma jet it was possible to reduce the ozone concentration in a working gas.

Hence, with the previously described embodiments, the ozone concentration in the air flow conveyed in the piping system can be reduced in a targeted manner by means of the device for reducing an ozone concentration, in particular by means of the ceramic filter and/or activated carbon filter and/or the plasma nozzle. As a result, the ozone concentration can be reduced to a value below a certain threshold value, in particular to a value below 0.1 ppm of ozone, within the ventilation system at the end of a cleaning operation, so that in a subsequent normal operation unpleasant smells and health hazards due to ozone released into the room to be supplied are reduced.

An effective reduction in the ozone concentration can in particular be achieved by a combination of the plasma jet with at least one ceramic filter and/or activated carbon filter. Therefore, the ventilation system preferably comprises both a plasma nozzle and one or more ceramic filters and/or activated carbon filters.

According to a further embodiment, the ventilation system has a control which is configured to operate the device for reducing an ozone concentration, in particular the plasma nozzle, for a pre-specified period at the end of a cleaning operation. According to a corresponding embodiment of the method, during a first period of time of the cleaning operation reactive oxygen species are generated by means of the generating unit and are fed to an air flow conveyed in the piping system and during a second period of time of the cleaning operation the air flow conveyed in the piping system is at least partly fed to the device for reducing an ozone concentration, in particular to a plasma nozzle for generating an atmospheric plasma jet as working gas.

In this way, it is ensured that the ozone concentration is reduced within the ventilation system at the end of the cleaning operation. Preferably, the generating unit is switched off for the pre-specified period of time at the end of the cleaning operation, so that no new ozone is produced by the generating unit. The pre-specified period of time preferably comprises a time span in the range from 3 to 20 minutes, preferably from 5 to 10 minutes.

According to a further embodiment, the ventilation system is designed as an air-conditioning system and has a heat exchanger which is configured to cool an air flow conveyed in a piping system during normal operation and the generating unit is arranged and configured in such a way that reactive oxygen species generated by means of the generating unit reach the heat exchanger.

In the case of air-conditioning systems, the risk of contamination by germs is particularly high in the area of the heat exchanger, since the heat exchanger has a high surface area, in order to improve the heat transfer, and which is particularly susceptible to contamination by germs. In particular, such heat exchangers typically have cooling elements, such as fins, which have a high surface area.

Therefore, the generating unit is preferably arranged and configured in such a way that reactive oxygen species generated by means of the generating unit in particular reach the area of the fins or cooling element of the heat exchanger. Further preferably, the generating unit is arranged and configured in such a way that in the cleaning operation in the area of the heat exchanger, in particular in the area of the cooling element or of the fins, a concentration of reactive species, in particular of ozone, of at least 7 g/m$^3$, preferably of at least 10 g/m$^3$, is achieved.

According to a further embodiment, the ventilation system has a plurality of generating units which are each configured to generate reactive oxygen species during a cleaning operation and to feed the generated reactive oxygen species to an air flow conveyed in the piping system and the ventilation system has a control which is configured to operate the generating units alternately during a cleaning operation.

By providing a plurality of generating units and decentralised generation of reactive oxygen species brought about as a result, it is possible to achieve a concentration of reactive oxygen species, in particular of ozone, which is sufficiently high, preferably at least 7 g/m$^3$, further preferably at least 10 g/m$^3$, in the whole piping system during the cleaning operation. In particular, this embodiment is suitable for multi-part piping systems, in which there is a plurality of air flows or a plurality of paths for the air flows.

By alternately activating the generating units, the power required for operating the ventilation system can be reduced. By in each case activating only one or a low number of generating units at the same time, the power required for operating the generating units amounts to less than that of the multiple, corresponding to the number of generating units, of the input power of a single generating unit. In this way, the power supply unit provided for supplying the generating units can be smaller in size, so that the costs of the ventilation system are reduced.

According to a further embodiment, the ventilation system has a control which is configured to carry out the above described method for operating a ventilation system or a described embodiment of this method. In the present case and in the whole application, a control is in particular understood as an electronic control which, for example, comprises a microprocessor and an associated memory with commands, wherein the execution of the commands by the processor causes execution of the provided control, in particular of the above described method or an embodiment thereof. The ventilation system can be largely automated by means of such a control, so that human interventions or maintenance are not required anymore. In particular, in this way an automatic cleaning operation can be carried out, so that the risk of contamination of the ventilation system or air-conditioning system by germs is reduced.

The ventilation system can be installed in a stationary fixed position, for example in a building such as a hospital or a laboratory. Alternatively, the ventilation system can be designed to be mobile, so that it can be installed and operated at different places, for example, or so that it can be attached to different rooms.

According to a further embodiment, the outlet of the piping system is attached to a ventilation opening of a room. This embodiment therefore relates to an (immobile or mobile) ventilation system in an installed state which is attached to the room to be supplied. The room is preferably a room of a building, in particular an operating theatre, a quarantine room on an isolation ward (isolation unit), a clean room or a laboratory room. The room can also be an interior of a closed device, such as an interior of a laboratory device (in particular of an incubator for cell and tissue cultures) or of a household appliance (in particular of a refrigerator etc.). In the case of such rooms, pollution or contamination with germs of ventilation systems or air-conditioning systems is particularly critical, so that the present invention provides advantages particularly for such rooms. In addition, times when such rooms are out of use typically generate considerable costs, so that by saving on maintenance times through the cleaning operation of the ventilation system, which preferably takes place automatically, considerable costs can be saved. In particular, the ventilation system can also be used to at least partly disinfect or sterilise the attached room.

Correspondingly, the above mentioned object is also achieved according to the invention by the use of the previously described ventilation system or of one of the described embodiments thereof for ventilating and/or air-conditioning a room of a building, in particular an operating theatre, a quarantine room on an isolation ward (isolation unit), a clean room or a laboratory room, or an interior of a closed device, such as an interior of a laboratory device (in particular of an incubator for cell and tissue cultures) or of a household appliance (in particular of a refrigerator etc.).

The above mentioned object is furthermore achieved by a generating unit for generating reactive oxygen species, in particular for use with a previously described ventilation system, having a gas inlet which is configured to feed in a working gas and having a gas outlet which is configured to release the working gas or the reactive oxygen species, wherein the generating unit is configured to generate reactive oxygen species during a generating operation by means of an electrical discharge in a working gas fed in through the gas inlet, preferably by means of a dielectric barrier discharge, and wherein the generating unit is further configured to generate an atmospheric plasma jet during a neutralisation operation by generating an arc discharge by applying a high-frequency high voltage between two electrodes in the working gas fed in through the gas inlet.

Such a generating unit is particularly suitable for being integrated into the previously described ventilation system. By installing the generating unit for generating reactive oxygen species, the reactive oxygen species required for cleaning or disinfecting the ventilation system can be generated using the generating unit. On the other hand, the ozone concentration within the working gas can be reduced by means of the generating unit for an atmospheric plasma jet integrated into the same generating unit, so that, for example, at the end of a cleaning operation an ozone concentration can be achieved which is below the pre-specified threshold value.

According to a further embodiment of the generating unit it has a first generating section which is configured to generate reactive oxygen species during a generating operation by means of an electrical discharge in a working gas fed in through the gas inlet, preferably by means of a dielectric barrier discharge, and the generating unit has a second generating section which is arranged between the first generating section and the gas outlet and is configured to generate an atmospheric plasma jet during a neutralisation operation by generating an arc discharge by applying a high-frequency high voltage between two electrodes in the working gas fed in through the gas inlet.

The above described generating unit, or an embodiment thereof, is preferably used as the generating unit of the above described ventilation or air-conditioning system. Preferably, the control of the ventilation system is configured to operate the generating unit in the generating operation in a first period of time of a cleaning operation of the ventilation system and is configured to operate the generating unit in the neutralisation operation in a second period of time of the cleaning operation, preferably at the end of a cleaning operation.

Further features and advantages of the invention emerge from the following description of several exemplary embodiments, in which reference is made to the attached figures.

DETAILED DESCRIPTION OF THE INVENTION

Figure 1A:
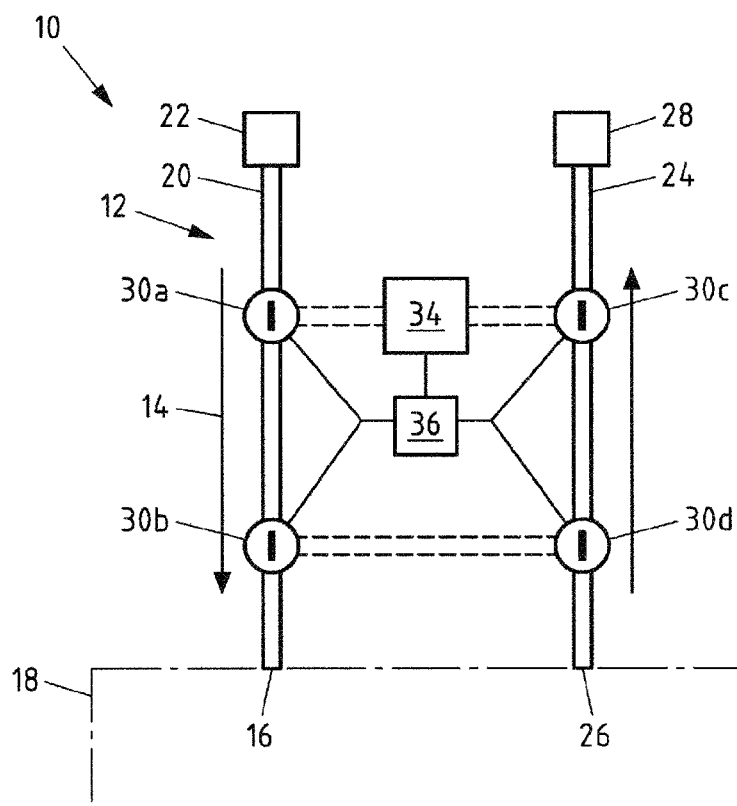
FIGS. 1a-b show a first exemplary embodiment of the ventilation system and of the method for operating it in a schematic illustration.
Figure 1B:
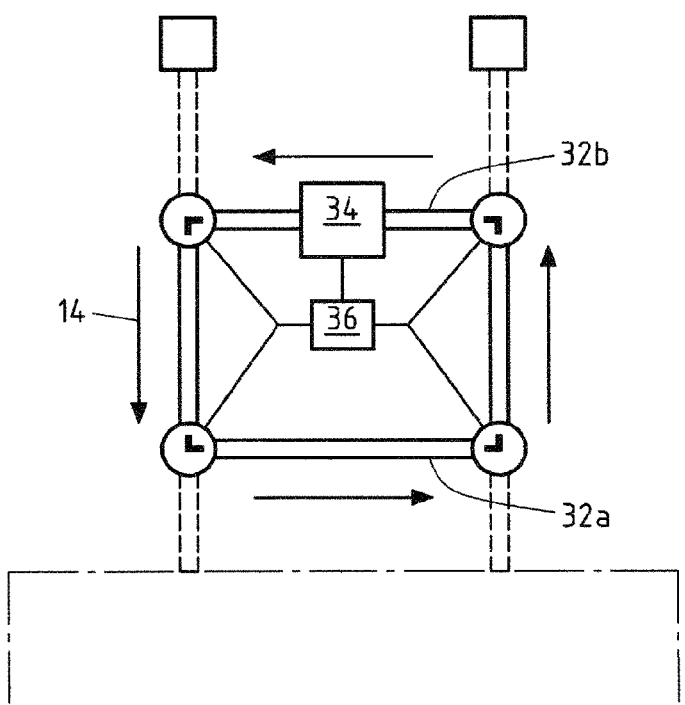

FIGS. 1a-b show a first exemplary embodiment of a ventilation system and a method for operating it in a schematic illustration.

The ventilation system 10 has a piping system 12 which is configured to convey an air flow 14 and to provide the air flow via an outlet 16 of the piping system 12 for supplying a room 18 during a normal operation.

For this purpose, the piping system 12 comprises a first pipe 20 which runs from an intake opening 22 to the outlet 16 which, for example, can be attached to a ventilation opening of the room 18. In addition, the piping system 12 comprises a second pipe 24 which runs from an inlet 26, which for instance can be attached to another ventilation opening of the room 18, to the outlet opening 28.

In the normal operation, the air flow 14 is sucked in through the intake opening 22 by a rotor (not illustrated) arranged in the pipe 20, conveyed through the pipe 20 and fed into the room 18 via the outlet 16 as supply air. In addition, the air flow 14 is sucked through the inlet 26 by a rotor (not illustrated) arranged in the pipe 24, conveyed through the pipe 24 and conducted out of the ventilation system 10 through the outlet opening 28. Thusly, the room 18 can be supplied with fresh air by means of the pipe 20 and spent air can be sucked out of the room 18 by means of the pipe 24.

The piping system 12 can be switched between an air supply mode (FIG. 1a) and an air circulation mode (FIG. 1b). For this purpose, the piping system 12 has controllable air guiding elements 30a-d and connection pipes 32a-b, by means of which the air flow 14 can be redirected, so that it can circulate within the piping system 12. The air guiding elements 30a-d can, for example, have controllable valves, by means of which alternately a way through to the first or second pipe 20, 24 or to one of the connection pipes 32a-b can be opened or closed, so that sections of the first or second pipe 20, 24 or of the connection pipes 32a-b can be unblocked or blocked for the air flow 14.

In the FIGS. 1a-b, the sections of the piping system 12 unblocked for the air flow 14 by the air guiding elements 30a-d are illustrated with continuous lines and the sections of the piping system 12 blocked for the air flow 14 by the air guiding elements 30a-d are illustrated with dashed lines. Preferably, the piping system has a rotor in a section of the first and/or second pipe 20, 24 which is unblocked both in the air supply mode and in the air circulation mode.

The ventilation system 10 also has a generating unit 34 which is configured to generate reactive oxygen species during a cleaning operation and to feed them to the air flow 14 conveyed in the piping system 12.

In the case of the ventilation system 10, the generating unit 34 is integrated into the connection pipe 32b.

In addition, the ventilation system has a control 36, by means of which the air guiding elements 30a-d and the generating unit 34 can be controlled. The control 36 is configured in such a way that the ventilation system 10, on the one hand, can be operated in a normal operation and, on the other hand, can be operated in a cleaning operation.

In the normal operation, the air guiding elements 30a-d are switched by the control 36 as illustrated in FIG. 1a, so that the ventilation system 10 is set up to supply air to or return air from the room 18. In the cleaning operation, on the other hand, the air guiding elements 30a-d are switched by the control 36 as illustrated in FIG. 1b, so that the air flow 14 can circulate within the piping system 12. In addition, the control 36 activates the generating unit 34 in the cleaning operation, so that it generates reactive oxygen species and feeds them to the circulating air flow 14. The generating unit 34 is controlled in such a way that a concentration of reactive oxygen species, in particular of ozone, of at least 7 g/m$^3$ (for a disinfection) or of at least 10 g/m$^3$ (for a sterilisation) is achieved in the air flow 14. The ventilation system 10 can be disinfected or even sterilised in this way.

Figure 2A:
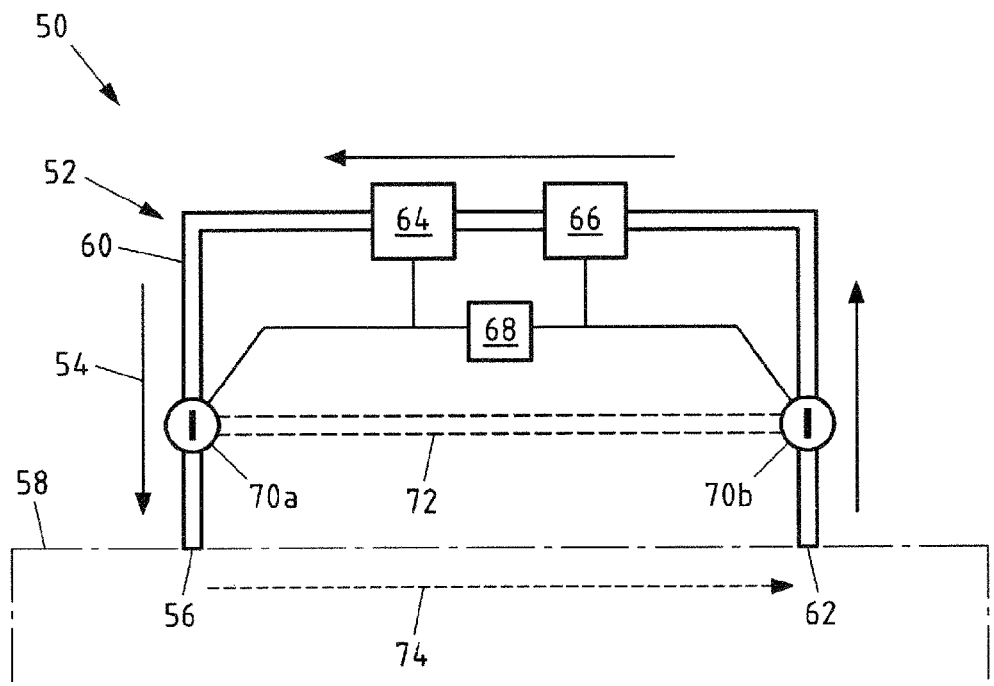
FIGS. 2a-2b show a second exemplary embodiment of the ventilation system and of the method for operating it in a schematic illustration.
Figure 2B:
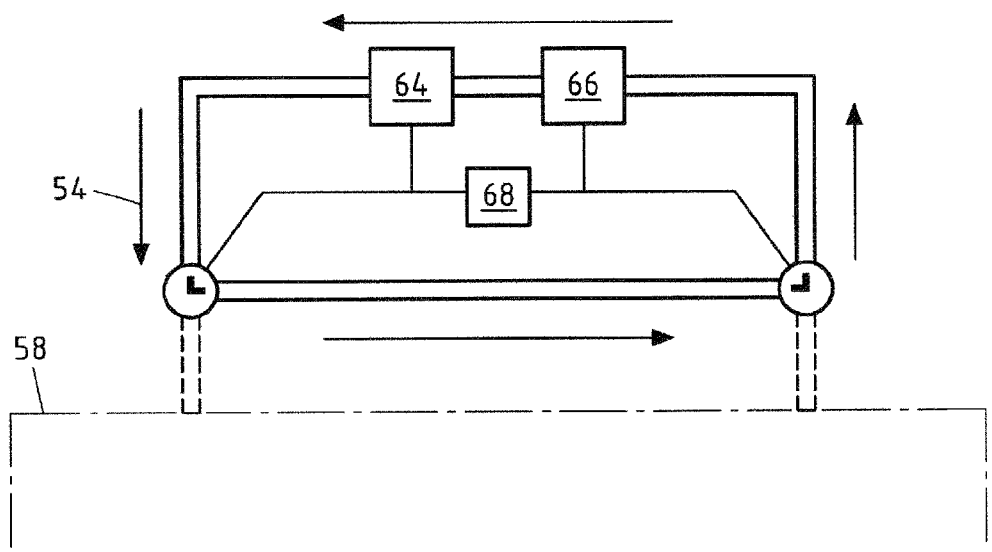

FIGS. 2a-2b show a further exemplary embodiment of a ventilation system, which in the present case is designed as an air-conditioning system. The ventilation system 50 has a piping system 52 which is configured to provide an air flow 54 via an outlet 56 of the piping system 52 for supplying a room 58 during a normal operation.

The ventilation system 50 designed as an air-conditioning system is in the present case only configured for cooling. Alternatively, the ventilation system can additionally also be configured to supply fresh air or remove spent air.

The piping system 52 comprises a main pipe 60 which runs from an inlet 62, which for example can be attached to a ventilation opening of the room 58, to a heat exchanger 64 and from there on to the outlet 56 which can be attached to a further ventilation opening of the room 58.

In the normal operation, an air flow 54 is sucked in through the inlet 62 by means of a rotor (not illustrated) arranged in the main pipe 60, conveyed through the main pipe 60 to the heat exchanger 64, by means of which the air flow 54 is cooled, and conveyed further through the outlet 56 into the room 58, so that this room 58 is air-conditioned by the cooled air flow 54.

The ventilation system 50 also has a generating unit 66 which is configured to generate reactive oxygen species during a cleaning operation and feed them to the air flow 54. In addition, the ventilation system 50 comprises another control 68 which is configured to control the generating unit 66. In particular, the control 68 is configured to operate the generating unit 66 during the cleaning operation in such a way that a concentration of reactive oxygen species, in particular of ozone, of at least 7 g/m$^3$ (for a disinfection) or of at least 10 g/m$^3$ (for a sterilisation) is achieved in the air flow 54. In this way, in the cleaning operation a disinfection or even a sterilisation of the ventilation system 50 is carried out. The generating unit 66 is preferably arranged in the flow direction of the air flow 54 upstream of the heat exchanger 64, so that the reactive oxygen species generated by the generating unit 66 reach the heat exchanger 64 in a concentration which is sufficient for a disinfection or sterilisation and disinfect or sterilise its surface, in particular the surface of cooling elements, such as fins, of the heat exchanger 64.

The piping system 52 can preferably be switched between an air supply mode (FIG. 2a) and an air circulation mode (FIG. 2b). For this purpose, the piping system 52 has controllable air guiding elements 70a-b and a connection pipe 72, by means of which the air flow 54 can be redirected, so that it can circulate within the piping system 52. The air guiding elements 70a-b can, for example, have controllable valves, by means of which alternately a way through to the main pipe 60 or to the connection pipe 72 can be opened or closed, so that sections of the main pipe 60 or of the connection pipe 72 can be unblocked or blocked for the air flow 54. The air guiding elements 70*a-b* are controlled via the control 68.

In FIGS. 2*a-b*, the sections of the piping system 52 unblocked for the air flow 54 by the air guiding elements 70*a-b* are illustrated with continuous lines and the sections of the piping system 52 blocked for the air flow 54 by the air guiding elements 70*a-b* are illustrated with dashed lines. Preferably, the piping system has a rotor in a section of the main pipe 60 which is unblocked both in the air supply mode and in the air circulation mode.

In the normal operation, the air guiding elements 70*a-b* are switched by the control 68 as illustrated in FIG. 2*a*, so that the ventilation system 50 is set up to air-condition the room 58. In the cleaning operation, on the other hand, the air guiding elements 70*a-b* are switched by the control 68 as illustrated in FIG. 2*b*, so that the air flow 54 can circulate within the piping system 52. In addition, the control 68 activates the generating unit 68 in cleaning operation, so that it generates reactive oxygen species and feeds them to the circulating air flow 54. The generating unit 66 is controlled in such a way that a concentration of reactive oxygen species, in particular of ozone, of at least 7 $g/m^3$ (for a disinfection) or of at least 10 $g/m^3$ (for a sterilisation) is achieved in the air flow 54, so that the ventilation system 50 and in particular the heat exchanger 64 can be disinfected or even sterilised.

Alternatively, the control 68 can also operate the ventilation system 50 in air supply mode (FIG. 2*a*) during the cleaning operation. The circular flow of the air flow 54 can then be closed via an air flow 74 flowing in the room 58. With this embodiment, the reactive oxygen species generated by the generating unit 66 also get into the room 58, so that in this way the room 58 can also be at least partly disinfected or sterilised. The room 58 can, for example, be a room of a building, in particular an operating theatre, a quarantine room on an isolation ward (isolation unit), a clean room or a laboratory room. The room can also be an interior of a closed device, such as an interior of a laboratory device (in particular of an incubator for cell and tissue cultures) or of a household appliance (in particular of a refrigerator etc.) an operating theatre, which in this way can be at least partly disinfected or even sterilised.

Figure 3:
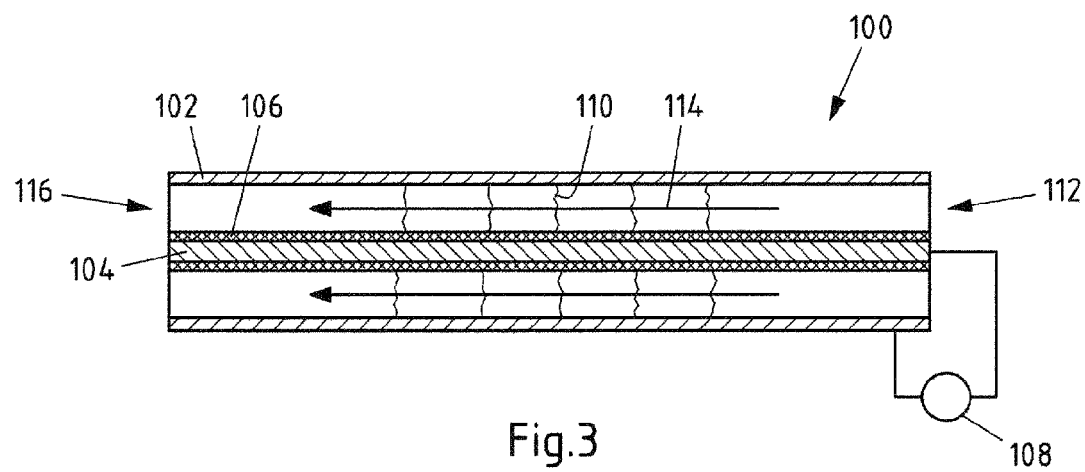
FIG. 3 shows a generating unit for generating reactive oxygen species in a schematic cross-sectional illustration.

FIG. 3 shows an exemplary embodiment of a generating unit 100 for generating reactive oxygen species. For example, the generating units 34 and 70 of the ventilation systems 10 and 50 can be designed like the generating unit 100.

The generating unit 100 has an outer electrode in the form of a metal tube 102 and an inner electrode in the form of a metal bar 104. The inner electrode is enclosed by a layer consisting of a dielectric material 106, for example a ceramic, so that the inner electrode 104 is electrically insulated with respect to the outer electrode 102.

A high frequency high voltage is applied between the inner electrode 104 and the outer electrode 102 by means of a voltage source 108 provided for this purpose. No direct electrical discharges between the inner electrode 104 and the outer electrode 102 are possible due to the dielectric layer 106. Therefore, so-called dielectric barrier discharges 110 occur between the electrodes 102, 104 during operation of the generating unit 100.

The generating unit 100 has a gas inlet 112 on the one side, through which a working gas 114 containing oxygen, in particular air, can reach the generating unit 100. Reactive oxygen species form as a result of the interaction of the working gas 114 with the discharges 110 and flow with the rest of the working gas 114 out of the gas outlet 116 of the generating unit 100.

The generating unit 100 can be arranged in a ventilation system like the ventilation system 10 or 50, for example, in such a way that the gas inlet 112 is flowed into by an air flow, such as the air flow 14 or 54. Additionally, a rotor can also be provided to direct the air flow into the gas inlet 112. The generating unit 100 is further arranged in the ventilation system such that the reactive oxygen species flowing out of the gas outlet 116 again get into the piping system of the ventilation system or into the air flow conveyed there, respectively.

It has been determined that reactive oxygen species can be generated in a sufficient amount and of sufficient reactivity to disinfect or to sterilise a ventilation system using a generating unit of the type described in FIG. 3.

In addition to other reactive oxygen species, non-inconsiderable quantities of ozone are also formed using the generating unit 100 illustrated in FIG. 3. Ozone has a relatively long half-life in air before it is transformed into other products. Therefore, at the end of a cleaning operation, the ozone can result in a health hazard and/or unpleasant smell in the room supplied by the ventilation system.

Therefore, in another exemplary embodiment of the ventilation system, in particular of the ventilation systems 10 and 50, a plasma nozzle for generating an atmospheric plasma jet can be provided, into which the air flow conveyed in the ventilation system, in particular the air flow 14 or 54, is conveyed as working gas. In this way, the ozone concentration in the working gas and hence in the air flow conveyed in the ventilation system can be reduced, preferably to a concentration below 0.1 ppm.

Figure 4:
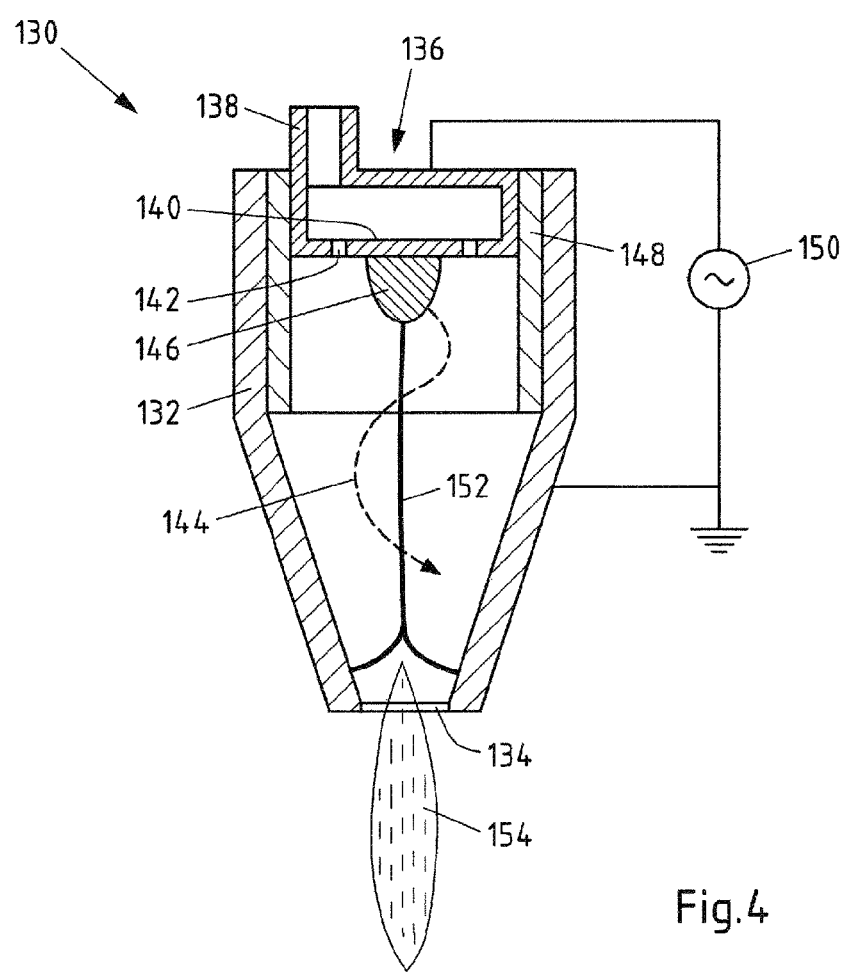
FIG. 4 shows a plasma nozzle for generating an atmospheric plasma jet in a schematic cross-sectional illustration.

FIG. 4 shows an exemplary embodiment of such a plasma nozzle.

The plasma nozzle 130 has a nozzle tube 132 made of metal which tapers essentially conically to form a nozzle tube opening 134. At the end opposite the nozzle tube opening 134, the nozzle tube 132 has a swirl device 136 with an inlet 138 for a working gas.

An intermediate wall 140 of the swirl device 136 has a ring of holes 142 set obliquely in the peripheral direction, through which the working gas is swirled. The downstream, conically tapered part of the nozzle tube 132 is therefore flowed through by the working gas in the form of a vortex 144, the core of which runs on the longitudinal axis of the nozzle tube 132.

An electrode 146 is arranged centrally on the underside of the intermediate wall 140 and protrudes coaxially into the nozzle tube 132 in the direction of the tapered section. The electrode 146 is electrically connected to the intermediate wall 140 and the other parts of the swirl device 136. The swirl device 136 is electrically insulated against the nozzle tube 132 by a ceramic tube 148. A high-frequency high voltage, which is generated by a transformer 150, is applied to the electrode 146 via the swirl device 136.

The inlet 138 is in particular arranged in such a way that a part of the air flow 14 or 54, respectively, can get into the plasma nozzle 130. The nozzle tube 132 is earthed. A high-frequency discharge in the form of an arc 152 is generated between the electrode 146 and the nozzle tube 132 by means of the applied voltage.

The terms "arc" or "arc discharge" are in the present case used as a phenomenological description of the discharge, since the discharge occurs in the form of an arc. The term "arc" is elsewhere also used as a form of discharge in the case of direct current voltage discharges with essentially constant voltage values. In the present case, however, it refers to a high-frequency discharge in the form of an arc, that is to say, a high-frequency arc discharge.

This arc 152 is channeled in the vortex core on the axis of the nozzle tube 132 due to the swirling flow of the working gas, so that it only branches out towards the wall of the nozzle tube 132 in the area of the nozzle tube opening 134.

The working gas, which rotates at high flow velocity in the area of the vortex core and hence in the immediate vicinity of the arc 152, comes into close contact with the arc 152 and is thereby partly converted into the plasma state, so that an atmospheric plasma jet 154 exits from the plasma nozzle 130 through the nozzle tube opening 134.

It has become apparent that the ozone concentration in a gas can be considerably reduced by conveying the gas as a working gas into the plasma nozzle 130. By exciting the working gas by means of the discharge 152, ozone molecules are broken down or transformed into other molecules, so that the ozone concentration of the working gas or plasma jet leaving the plasma nozzle 130 is lower than the ozone concentration of the working gas conveyed into the plasma nozzle 130.

Therefore, the plasma nozzle 130 illustrated in FIG. 4 can be advantageously used in the ventilation system 10 or 50 to reduce the ozone concentration at the end of a cleaning operation and thereby prevent impairment to health or smell pollution owing to the ozone.

Additionally or as an alternative to such a plasma nozzle, activated carbon filters and/or ceramic filters (not illustrated) can also be installed in the ventilation system to reduce the ozone concentration at the end of a cleaning operation.

Figure 5:
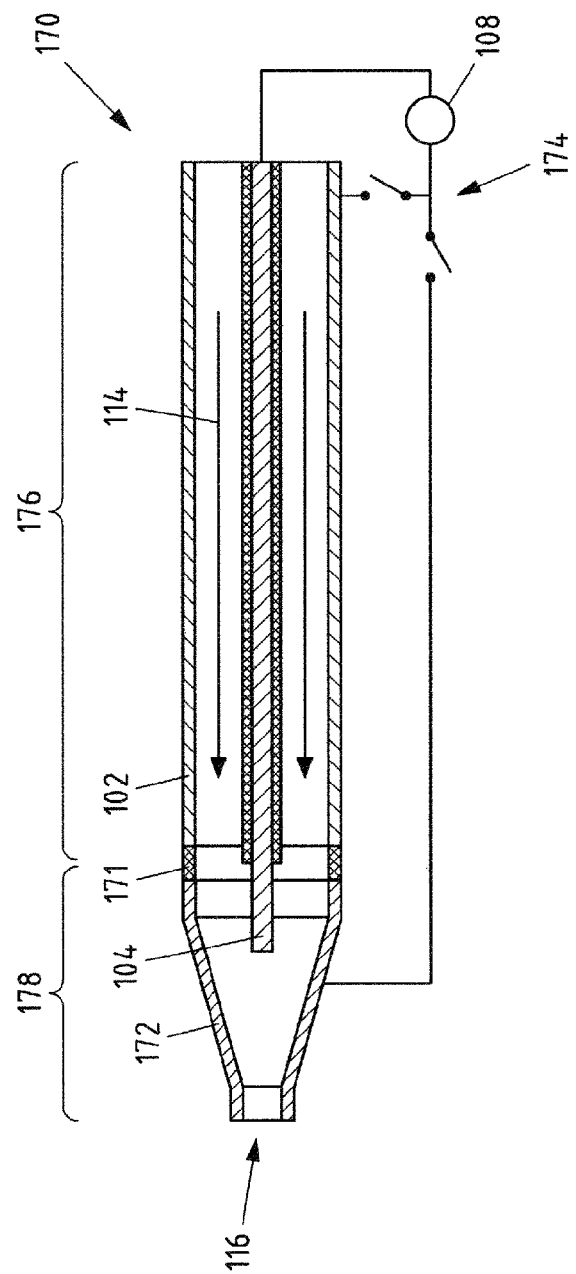
FIG. 5 shows an exemplary embodiment of a generating unit for generating reactive oxygen species, in particular for use with a ventilation system.

A plasma nozzle for generating an atmospheric plasma jet can also be advantageously integrated into the generating unit. FIG. 5 shows an exemplary embodiment of such a generating unit 170, the construction of which is similar to the generating unit 100 from FIG. 3. The same components are in each case provided with the same reference symbols.

The generating unit 170 differs from the generating unit 100 by the fact that the inner electrode 104 on the end facing the gas outlet 116 is extended beyond the dielectric layer 106 and that it has a second outer electrode 172 electrically insulated from the first outer electrode 102 by an insulator 171 and tapering to form a nozzle opening in the area of the gas outlet 116. The second outer electrode 172 is also attached to the voltage source 108. The first and/or the second outer electrode 102, 172 can in each case be connected via provided switches 174.

The generating unit 170 thusly has a first generating section 176 which is configured to generate reactive oxygen species and a second generating section 178 which—comparable with the plasma jet 130 in FIG. 4—is configured to generate an atmospheric plasma jet. The ozone concentration in the working gas 114 can be reduced by means of the second generating section 178.

Figure 6:
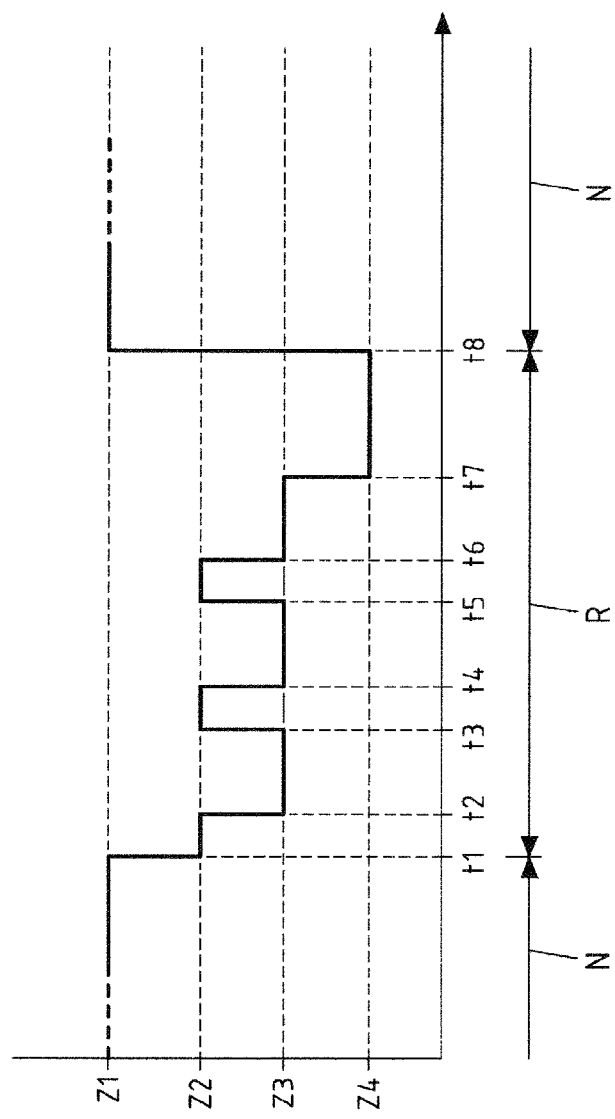
FIG. 6 shows a control diagram corresponding to an exemplary embodiment of the method for operating a ventilation system.

FIG. 6 shows a control diagram corresponding to an exemplary embodiment of the method for operating a ventilation system, in particular the ventilation system 10 or 50.

Four states Z1 to Z4 of the ventilation system to be controlled in each case, which are switched between by means of the control of the ventilation system, in particular by means of the control 36 or 72, at pre-specified times t1 to t8, are plotted in the diagram. The state Z1 corresponds to a normal operation and the states Z2 to Z4 correspond to different states in the cleaning operation of the ventilation system. The meaning of the individual states Z1 to Z4 is described below.

Z1: In this state, the ventilation system runs in the normal operation, so that an air flow conveyed in the piping system is provided via an outlet of the piping system for supplying a room.

Z2: In this state, the control activates the generating unit of the ventilation system, so that it generates reactive oxygen species and introduces them into an air flow conveyed in the piping system of the ventilation system. This state is also referred to as the activation period.

Z3: In this state, the generating unit is switched off, so that no further reactive oxygen species are generated. This state is also referred to as the decaying period.

Z4: In this state, a plasma nozzle integrated into the ventilation system is activated, so that the ozone concentration of the air flow conveyed in the piping system is reduced. The generating unit is preferably deactivated in this state.

The diagram in FIG. 6 now shows an exemplary process sequence of a control of the ventilation system between the above mentioned states Z1-Z4.

According to this, the control can be configured in such a way that it switches the ventilation system at a pre-specified time t1 from a normal operation N to a cleaning operation R. In the present case, the cleaning operation lasts from the time t1 to the time t8 and can, for example, span a period of one to two hours. Switching from the normal operation N to the cleaning operation preferably takes place at a time at which the room supplied by the ventilation system is not being worked in, for example at night.

At time t1, the control preferably switches the piping system to air circulation mode, so that an air flow can circulate within the piping system. Then, the control operates the generating unit from time t1 to t7, preferably in phases, wherein the generating unit is activated for activation periods (from t1 to t2, from t3 to t4 and from t5 to t6) respectively, so that it generates reactive oxygen species and introduces them into the air flow in the piping system, and wherein the generating unit in decaying periods in between (from t2 to t3, from t4 to t5 and from t6 to t7) is switched off.

Towards the end of the cleaning operation, the control switches the ventilation system to a neutralisation operation (from t7 to t8), in which the generating unit is switched off and the plasma nozzle for generating atmospheric plasma jet is switched on, in order to reduce the ozone concentration within the ventilation system.

At the end of the cleaning operation at time t8, the control automatically switches the ventilation system to normal operation again, so that the ventilation system keeps on running.

This method of operation enables the ventilation system to be regularly and automatically disinfected or sterilised without time-consuming maintenance work being required for this purpose.

The invention claimed is:

1. A ventilation system, comprising a piping system which is configured to convey an air flow and to provide the air flow via an outlet of the piping system for supplying a room during a normal operation,
    wherein the ventilation system is designed as an air-conditioning system and has a heat exchanger which is configured to cool the air flow conveyed in the piping system during the normal operation, wherein
    the ventilation system has a generating unit, which is configured to generate reactive oxygen species during a cleaning operation and to feed the reactive oxygen species to the air flow conveyed in the piping system, wherein the generating unit is configured to generate the reactive oxygen species by means of an electrical discharge in a working gas, and wherein the generating unit is arranged and configured in such a way that the reactive oxygen species generated by means of the generating unit reach the heat exchanger, wherein the ventilation system comprises a plasma nozzle for generating an atmospheric plasma jet, wherein the plasma nozzle is configured to generate the plasma jet by generating an arc discharge by applying a high-frequency high voltage between two electrodes in a working gas, wherein the generating unit and the plasma nozzle share at least one electrode for the purposes of generating the electrical discharge and the plasma jet, and the piping system and the plasma nozzle are configured in such a way that the air flow conveyed in the piping system can be fed to the plasma nozzle as working gas, wherein the ventilation system further comprises a control, and during the cleaning operation, the control is configured to:

activate the generating unit at a start of the cleaning operation to initiate a first stage of the cleaning operation, wherein the first stage of the cleaning operation comprises alternating between activation periods during which the generating unit is activated and decay periods during which the generating unit is deactivated, wherein the plasma nozzle is deactivated during the first stage; and deactivate the generating unit and activate the plasma nozzle to initiate a final stage of the cleaning operation for a pre-determined period of time at the end of the cleaning operation.

2. The ventilation system according to claim 1, wherein the control is configured to control the generating unit during the first stage of the cleaning operation in such a way that during the cleaning operation a concentration of the reactive oxygen species of at least 7 g/m3 is achieved in the air flow conveyed in the piping system.

3. The ventilation system according to claim 1, wherein the control is configured to operate the ventilation system in the cleaning operation at pre-specified times or for pre-specified periods.

4. The ventilation system according to claim 1, wherein the piping system is switchable between an air supply mode and an air circulation mode, wherein the piping system in the air supply mode is configured to provide the air flow conveyed in the piping system via the outlet for supplying the room, and wherein the piping system in the air circulation mode is configured to circulate the air flow conveyed in the piping system within the piping system.

5. The ventilation system according to claim 1, wherein the ventilation system has a plurality of generating units which are each configured to generate the reactive oxygen species during the cleaning operation and to feed the generated reactive oxygen species to the air flow conveyed in the piping system, and wherein the control is configured to operate the generating units alternately during the cleaning operation.

6. The ventilation system according to claim 1, wherein the outlet of the piping system is attached to a ventilation opening of the room.

7. The ventilation system according to claim 1, wherein the ventilation system is in fluid communication with an interior of a closed space, the interior of the closed space comprising an interior of a laboratory device or a household appliance.

8. The ventilation system according to claim 7, wherein the laboratory device is an incubator.

9. The ventilation system according to claim 7, wherein the household appliance is a refrigerator.

10. A ventilation system comprising a piping system which is configured to convey an air flow and to provide the air flow via an outlet of the piping system for supplying a room during a normal operation, wherein the ventilation system is designed as an air-conditioning system and has a heat exchanger which is configured to cool the air flow conveyed in the piping system during the normal operation, wherein the ventilation system has a generating unit, which is configured to generate reactive oxygen species during a cleaning operation and to feed the reactive oxygen species to the air flow conveyed in the piping system, wherein the generating unit is configured to generate the reactive oxygen species by means of an electrical discharge in a working gas, and wherein the generating unit is arranged and configured in such a way that the reactive oxygen species generated by means of the generating unit reach the heat exchanger, the ventilation system further configured to convey the air flow in the piping system;

and to supply the air flow to the room via the outlet during the normal operation, wherein, during the cleaning operation, reactive oxygen species are generated by means of the generating unit and are fed to the air flow conveyed in the piping system, wherein the ventilation system comprises a plasma nozzle for generating an atmospheric plasma jet, wherein the plasma nozzle is configured to generate the plasma jet by generating an arc discharge by applying a high-frequency high voltage between two electrodes in a working gas, and wherein the piping system and the plasma nozzle are configured in such a way that the air flow conveyed in the piping system can be fed to the plasma nozzle as working gas, wherein the generating unit and the plasma nozzle share at least one electrode for the purposes of generating the reactive oxygen species and the plasma jet, and wherein the ventilation system comprises a control, and during the cleaning operation, the control is configured to:

activate the generating unit at a start of the cleaning operation to initiate a first stage of the cleaning operation, wherein the first stage of the cleaning operation comprises alternating between activation periods during which the generating unit is activated and decay periods during which the generating unit is deactivated, wherein the plasma nozzle is deactivated during the first stage; and deactivate the generating unit and activate the plasma nozzle to initiate a final stage of the cleaning operation for a pre-determined period of time at the end of the cleaning operation.

11. A method for operating a ventilation system comprising:
- conveying an air flow in a piping system; and
- supplying the air flow to a room via an outlet during a normal operation,
- wherein, during a cleaning operation, reactive oxygen species are generated by means of a generating unit and are fed to the air flow conveyed in the piping system, wherein
- the ventilation system comprises a plasma nozzle for generating an atmospheric plasma jet, wherein the plasma nozzle is configured to generate the plasma jet by generating an arc discharge by applying a high-frequency high voltage between two electrodes in a working gas, and wherein
- the piping system and the plasma nozzle are configured in such a way that the air flow conveyed in the piping system can be fed to the plasma nozzle as working gas,
- wherein the generating unit and the plasma nozzle share at least one electrode for the purposes of generating the reactive oxygen species and the plasma jet, and
- wherein the ventilation system comprises a control, and during the cleaning operation, the control is configured to:
  - activate the generating unit at a start of the cleaning operation to initiate a first stage of the cleaning operation, wherein the first stage of the cleaning operation comprises alternating between activation periods during which the generating unit is activated and decay periods during which the generating unit is deactivated, wherein the plasma nozzle is deactivated during the first stage; and
  - deactivate the generating unit and activate the plasma nozzle to initiate a final stage of the cleaning operation for a pre-determined period of time at the end of the cleaning operation.

12. The method according to claim 11, wherein during the cleaning operation the air flow is circulated within the piping system.

13. A generating unit for generating reactive oxygen species, comprising:
- a gas inlet which is configured to feed in a working gas and
- a gas outlet which is configured to release the working gas or the reactive oxygen species,
- wherein the generating unit has a first generating section which is configured to generate the reactive oxygen species during a generating operation by means of an electrical discharge in the working gas fed in through the gas inlet,
- wherein the generating unit has a second generating section which is arranged between the first generating section and the gas outlet and is configured to generate an atmospheric plasma jet during a neutralization operation by generating an arc discharge by applying a high-frequency high voltage between two electrodes in the working gas fed in through the gas inlet,
- wherein the generating unit and the plasma nozzle share at least one electrode for the purposes of generating the electrical discharge and the plasma jet, and
- wherein the generating unit is configured to communicate with a control configured to cause the generating unit during a cleaning operation to:
  - activate the first generating section at a start of the cleaning operation to initiate a first stage of the cleaning operation, wherein the first stage of the cleaning operation comprises alternating between activation periods during which the first generating section is activated and decay periods during which the first generating section is deactivated, wherein the second generating section is deactivated during the first stage, and
  - deactivate the first generating section and activate the second generating section to initiate a final stage of the cleaning operation for a pre-determined period of time at the end of the cleaning operation.

\* \* \* \* \*